US008886390B2

(12) United States Patent
Wolfe et al.

(10) Patent No.: US 8,886,390 B2
(45) Date of Patent: Nov. 11, 2014

(54) MONITORING, DIAGNOSTIC AND TRACKING TOOL FOR AUTONOMOUS MOBILE ROBOTS

(71) Applicant: Aethon, Inc., Pittsburgh, PA (US)

(72) Inventors: David G. Wolfe, Wexford, PA (US); George F. Lucas, Pittsburgh, PA (US); Mark Swaney, Pittsburgh, PA (US)

(73) Assignee: Aethon, Inc., Pittsburgh, PA (US)

( * ) Notice: Subject to any disclaimer, the term of this patent is extended or adjusted under 35 U.S.C. 154(b) by 72 days.

(21) Appl. No.: 13/624,373

(22) Filed: Sep. 21, 2012

(65) Prior Publication Data

US 2013/0085625 A1 Apr. 4, 2013

Related U.S. Application Data

(60) Provisional application No. 61/537,730, filed on Sep. 22, 2011.

(51) Int. Cl.
G01C 21/34 (2006.01)
G06F 19/00 (2011.01)
G06F 17/00 (2006.01)

(52) U.S. Cl.
CPC ............... *G06F 17/00* (2013.01); *G06F 19/00* (2013.01); *G06F 19/327* (2013.01)
USPC ............ 701/29.1; 701/1; 701/29.2; 701/29.3; 701/482; 701/522; 700/245; 700/247; 700/249; 700/255

(58) Field of Classification Search
None
See application file for complete search history.

(56) References Cited

U.S. PATENT DOCUMENTS

| 5,619,412 | A | * | 4/1997 | Hapka | 701/36 |
| 6,098,048 | A | * | 8/2000 | Dashefsky et al. | 705/7.32 |
| 6,150,961 | A | * | 11/2000 | Alewine et al. | 340/995.1 |
| 6,519,498 | B1 | | 2/2003 | Jevtic et al. | |
| 6,681,174 | B1 | * | 1/2004 | Harvey et al. | 701/117 |
| 7,100,725 | B2 | | 9/2006 | Thorne | |
| 7,431,115 | B2 | | 10/2008 | Thorne | |

(Continued)

OTHER PUBLICATIONS

Notification of Transmittal of the International Search Report and the Written Opinion of the International Searching Authority, International Search Report and Written Opinion of the International Searching Authority for PCT/US2012/056632, dated Nov. 30, 2012 (9 pages).

*Primary Examiner* — Thomas Tarcza
*Assistant Examiner* — Richard Goldman
(74) *Attorney, Agent, or Firm* — Buchanan Ingersoll & Rooney PC

(57) ABSTRACT

A system and method are provided for managing and prioritizing for action fleets of mobile robots deployed at various locations. The system/method includes a plurality of homebase servers, each corresponding to a different location, with each of the homebase servers receiving operational parameter data (representing operational and navigational issues experienced by the mobile robot) from a plurality of mobile robots operating at the particular location where the homebase server is deployed. A central server receives the operational parameter data from the plurality of homebase servers. The central server included a data analysis module for processing the operational parameter data and prioritizing the mobile robots operating at the various locations for action by support staff. A list is generated ranking the mobile robots in order of importance for action by support staff.

30 Claims, 12 Drawing Sheets

(56) References Cited

U.S. PATENT DOCUMENTS

| | | | |
|---|---|---|---|
| 7,894,939 B2* | 2/2011 | Zini et al. ................. 700/245 |
| 8,060,400 B2* | 11/2011 | Wellman ................... 235/375 |
| 8,078,485 B1* | 12/2011 | Kraehmueller et al. ..... 705/7.11 |
| 8,583,333 B2* | 11/2013 | Rennie et al. .............. 701/50 |
| 2002/0089962 A1* | 7/2002 | Lagoutte ..................... 370/338 |
| 2003/0130851 A1* | 7/2003 | Nakakita et al. ............ 704/275 |
| 2003/0163249 A1* | 8/2003 | Kapolka et al. ............. 701/123 |
| 2004/0019577 A1* | 1/2004 | Abdel-Malek et al. ........ 707/1 |
| 2004/0039504 A1* | 2/2004 | Coffee et al. ................ 701/35 |
| 2004/0077347 A1* | 4/2004 | Lauber et al. ............... 455/428 |
| 2004/0088115 A1* | 5/2004 | Guggari et al. ............. 702/13 |
| 2004/0138790 A1* | 7/2004 | Kapolka et al. ............. 701/29 |
| 2004/0236474 A1* | 11/2004 | Chowdhary et al. .......... 701/1 |
| 2005/0038580 A1* | 2/2005 | Seim et al. .................. 701/29 |
| 2005/0177761 A1* | 8/2005 | Martiniere ................... 714/4 |
| 2007/0118502 A1* | 5/2007 | Aragones et al. ............ 707/2 |
| 2007/0216521 A1* | 9/2007 | Guensler et al. ............. 340/439 |
| 2008/0059272 A1* | 3/2008 | Jeanneret et al. ............ 705/8 |
| 2008/0154691 A1* | 6/2008 | Wellman et al. ............. 705/9 |
| 2008/0154712 A1* | 6/2008 | Wellman ..................... 705/11 |
| 2009/0099898 A1* | 4/2009 | Ehrman et al. .............. 705/9 |
| 2009/0210081 A1* | 8/2009 | Sustaeta et al. ............. 700/99 |
| 2009/0234499 A1* | 9/2009 | Nielsen et al. .............. 700/250 |
| 2009/0327011 A1* | 12/2009 | Petroff ....................... 705/8 |
| 2010/0046436 A1* | 2/2010 | Doviak et al. ............... 370/328 |
| 2010/0094459 A1* | 4/2010 | Cho et al. ................... 700/248 |
| 2010/0205021 A1* | 8/2010 | Jewett et al. ................ 705/7 |
| 2010/0217638 A1* | 8/2010 | Dickson et al. .............. 705/7 |
| 2010/0228428 A1* | 9/2010 | Harshbarger et al. ......... 701/33 |
| 2010/0234991 A1 | 9/2010 | Zini et al. |
| 2010/0332133 A1* | 12/2010 | Harris et al. ................ 701/211 |
| 2011/0022442 A1* | 1/2011 | Wellman et al. ............. 705/9 |
| 2011/0029804 A1* | 2/2011 | Hadden et al. .............. 714/1 |
| 2011/0037565 A1* | 2/2011 | Skirble et al. ............... 340/8.1 |
| 2011/0040440 A1* | 2/2011 | de Oliveira et al. .......... 701/30 |
| 2011/0130906 A1* | 6/2011 | Mayer ........................ 701/22 |
| 2011/0137457 A1* | 6/2011 | Zini et al. ................... 700/245 |
| 2011/0137759 A1* | 6/2011 | Wellington et al. ........... 705/28 |
| 2011/0163160 A1* | 7/2011 | Zini et al. ................... 235/385 |
| 2011/0202591 A1* | 8/2011 | Reis et al. ................... 709/203 |
| 2011/0208357 A1* | 8/2011 | Yamauchi ................... 700/258 |
| 2011/0208567 A9* | 8/2011 | Roddy et al. ................ 705/7.41 |
| 2011/0288684 A1* | 11/2011 | Farlow et al. ............... 700/264 |
| 2011/0302019 A1* | 12/2011 | Proctor et al. .............. 705/14.27 |
| 2012/0092180 A1* | 4/2012 | Rikkola et al. .............. 340/679 |
| 2012/0136509 A1* | 5/2012 | Everett et al. ............... 701/2 |
| 2012/0232961 A1* | 9/2012 | Wellman et al. ............. 705/7.38 |
| 2012/0253888 A1* | 10/2012 | Davidson .................... 705/7.38 |
| 2013/0024060 A1* | 1/2013 | Sukkari et al. .............. 701/22 |
| 2013/0030873 A1* | 1/2013 | Davidson .................... 705/7.36 |
| 2013/0085625 A1* | 4/2013 | Wolfe et al. ................. 701/1 |
| 2013/0245883 A1* | 9/2013 | Humphrey ................... 701/36 |
| 2013/0311437 A1* | 11/2013 | Stluka et al. ................ 707/706 |

\* cited by examiner

| Device | Status | Battery | JobStart | Idle | Itinerary | Lock | NoComm | Service Tickets | Past Week | Claim (all) Hide |
|---|---|---|---|---|---|---|---|---|---|---|
| Tug-120-1 | Charging on Second Floor | 97% | 00:41:52 | 15:36:01 | | | 19:49:36 | 1 | 1 | ☐ |
| Tug-116-4 | Blocked on Lobby Floor | 91% | 00:02:37 | 00:00:59 | | HS | | 0 | 1 | C ☐ |
| Tug-39-3 | Waiting for other Tugs | 96% | 00:20:17 | 00:05:19 | 1South ✓ | 1NorthSouth | | 0 | 0 | C ☐ |
| Tug-113-1 | Navigating on First Floor | 96% | 00:33:08 | 00:01:12 | | DockHall | 00:02:45 | 0 | 0 | C ☐ |
| Tug-31-3 | Navigating on Basement | 100% | 00:01:31 | 00:01:08 | PharmOut,2Pharm,3Pharm,Pharmin | Pharm | | 0 | 0 | C ☐ |
| Tug-97-1 | Pushed on Basement | 96% | 00:31:51 | 00:26:31 | 5Trash1 | 5Trash1 | | 0 | 0 | C ☐ |
| Tug-80-2 | Blocked on Second Floor | 96% | 00:33:31 | 00:10:25 | 5East ✓,BCRC2 ✓ | | | 0 | 0 | C ☐ |
| Tug-98-3 | Waiting for other Tugs | 93% | 00:33:09 | 00:07:15 | Tram1 ✓,WWSS | Elev54_0(1) | | 0 | 0 | C ☐ |
| Tug-80-1 | Waiting for elevator on basement | 96% | 00:12:23 | 00:05:37 | BCRC1 | | | 0 | 0 | C ☐ |
| Tug-97-2 | Waiting At Destination: B Trash2 | 96% | 00:31:48 | 00:23:49 | BTrash2 | 5Trash2 | | 0 | 0 | C ☐ |
| Tug-97-3 | Waiting At Destination: B Trash3 | 96% | 00:31:45 | 00:22:34 | BTrash3 | 5Trash3 | | 0 | 0 | C ☐ |
| Tug-97-4 | Waiting At Destination: B Trash4 | 96% | 00:31:41 | 00:21:45 | BTrash4 | 5Trash4 | | 0 | 0 | C ☐ |
| Tug-97-5 | Waiting At Destination: B Linen5 | 96% | 00:24:29 | 00:10:52 | BLinenLoad ✓,BLinen5,BLinenUnload | 5Linen5 | | 0 | 0 | C ☐ |
| Tug-97-6 | Waiting At Destination: B Linen6 | 96% | 00:24:26 | 00:10:01 | BLinenLoad ✓,BLinen6,BLinenUnload | 5Linen6 | | 0 | 0 | C ☐ |
| Tug-97-7 | Waiting At Destination: B Linen7 | 96% | 00:24:23 | 00:09:50 | BLinenLoad ✓,BLinen7,BLinenUnload | 5Linen7 | | 0 | 0 | C ☐ |
| Device | Status | Battery | JobStart | Idle | Itinerary | Lock | NoComm | Service Tickets | Past Week | Claim (all) Hide |

Showing 1 to 15 of 15 entries (filtered from 283 total entries)

FIG. 5

| Color Legend | ✕ |
|---|---|
| Tug-X-0 | Tug's in MM greater than 12 hours |
| Tug-X-1 | Catch all on idle time. Tug is not at a destination and idle for more than 20 minutes, or no comm is greater than 15 minutes |
| Tug-X-2 | Zap Abort / Estopped Tugs |
| Tug-X-3 | Low Battery |
| Tug-X-4 | Tug is in an invalid state - Software Issue |
| Tug-X-5 | Tug idle at elevator for over 20 minutes |
| Tug-X-6 | The elevator the Tug is using is reporting unavailable |
| Tug-X-7 | Blocked tug, idle for more than 2 minutes OR Door, idle more than 5 minutes |
| Tug-X-8 | Tug-Cart Comm, Sensors Module, or Wall Localization failure |
| Tug-X-9 | Tug requires a reboot, look at "Alert Info" and follow instructions |
| Tug-X-10 | Medex related error, look at "Alert Info" and follow instructions |
| Tug-X-11 | Tunnel Down, we have not received a packet for over 5 minutes from this site |

FIG. 10

MONITORING, DIAGNOSTIC AND TRACKING TOOL FOR AUTONOMOUS MOBILE ROBOTS

CROSS-REFERENCE TO RELATED APPLICATIONS

This patent application claims the benefit of co pending U.S. Provisional Patent Application No. 61/537,730, filed on Sep. 22, 2011, the disclosure of which is hereby incorporated by reference in its entirety.

FIELD OF THE INVENTION

The present invention is directed toward the remote monitoring of autonomous mobile robots and, more particularly, toward the ranking and displaying of operation parameters for autonomous mobile robots for analysis and support by remote staff.

BACKGROUND OF THE INVENTION

Autonomous mobile robots and the software controlling them have steadily evolved in both complexity and functionality in recent years. Robotic and automated vehicles for delivering or transporting materials indoors (as well as outdoors) have been developed and utilized in a number of applications. For example, autonomous mobile robots have been developed for pulling carts or wagons which are useful in an industrial setting, such as hospitals and the like. The carts or wagons can include virtually any item required for delivery or retrieval. In a hospital setting, for example, such items can include, but are not limited to, lab work/results, blood, patient records, medications, emergency room (ER) materials/equipment, supplies, meals, etc. Alternately, the cart or cargo carrying area may be incorporated integrally with the autonomous mobile robot vehicle.

Such autonomous mobile robots are designed to be able to navigate alongside humans in real world situations, even when presented with complex and ever changing environments. For example, U.S. Pat. Nos. 7,100,725, 7,431,115 and 7,894,939, which are assigned to the owner of the present invention and are incorporated by reference herein in their entireties, describe exemplary autonomous mobile robotic vehicles that may be utilized or implemented in accordance with the inventive system and method described herein. However, other types of autonomous mobile robotic vehicles may also be utilized/implemented without departing from the spirit and scope of the present invention.

Although these autonomous mobile robotic systems are inherently stable, unpredictable situations are bound to, and do, arise that require human intervention to analyze and resolve. These situations include, among other things, robot idle time (e.g., no motion) which may be caused by facility issues such as, but not limited to, elevator delays, blocked pathways (e.g., obstacles in hallway), and failed equipment (e.g., automated doors not opening on command). Support personnel are typically located at a central location remote from the location(s) of the autonomous mobiles robot vehicles. Support personal will typically monitor and be responsible for any number of fleets of autonomous mobile robots deployed at various locations. In prior art systems, when an autonomous mobile robot encountered a navigation problem or obstacle that it could not navigate around, an e-mail was sent to the remote central support location reporting the problem. The support personal would then receive and read the e-mail, deduce the problem, and then could either take control of the autonomous mobile robot and navigate around the problem or, if necessary, contact appropriate individuals at the vehicle location who could address the problem. However, there are inherent problems with such a prior art approach.

During the time it takes for the remotely located support personnel to receive and read the e-mail, the autonomous mobile robot may have worked itself around the problem or obstacle and currently be continuing on its way. The support personnel would have no way of knowing this, except if the autonomous mobile robot sent another e-mail, which would only be received and read after the support personnel has wasted time trying to solve a problem that does not exist anymore. Additionally, the information contained in the e-mail may not be sufficient for the support personnel to figure out the problem that the autonomous mobile robot in encountering. This is simply because one cannot predict all of the problems and obstacles such a device may encounter. Further, when a plurality of autonomous mobile robot vehicles are encountering navigational problems at or near the same time, support personnel must be able to quickly and accurately figure out which problems are the most severe in order to address them first. Addressing navigational problems via an e-mail report system is often done on a first come first serve basis. Further still, it would be desirable to monitor navigation problems encountered by the various autonomous mobile robots at the various locations in order to analyze such problems to determine if certain areas of certain locations are experiencing a high volume of navigational issues. Modification of these areas at the location may help to alleviate problems going forward.

The presently described system and method is directed toward overcoming one or more of the above-mentioned problems. Although aspects of the inventive system and method will be described herein with reference to a preferred embodiment of a hospital setting, the inventive system and method may be applied in an endless variety of delivery-related applications in many environments (both indoor and outdoor) without departing from the spirit and scope of the present invention.

SUMMARY OF THE INVENTION

In accordance with the present invention, a system is provided for managing and prioritizing for action fleets of mobile robots deployed at various locations. The system includes a plurality of homebase servers, each corresponding to a different location, wherein each of the homebase servers receives operational parameter data from a plurality of mobile robots operating at the particular location where the homebase server is deployed. A central server receives the operational parameter data from the plurality of homebase servers, the central server including a data analysis module processing the operational parameter data and prioritizing the mobile robots operating at the various locations for action by support staff.

The operational parameter data represents operational and navigational issues experienced by the mobile robot. The data analysis module processes the operational data and prioritizes the mobile robots using a set of business rules. Typically, the business rules are location and mobile robot specific.

In prioritizing the mobile robots for action, the data analysis module generates a list prioritizing the mobile robots and ranking them in order of importance for action by support staff. The list generated by the data analysis module is generally accessed by the support staff using a web-based application. The list includes links to other information about the mobile robot and the location at which the mobile robot is operating, which can be used by the support staff to help in identifying the problem the mobile robot is experiencing and correcting the problem. The list generated by the data analysis module includes operational information about the mobile robot. In one form the operational information is color coded to identify potential critical issues.

As an additional feature, mobile robots appearing in the list generated by the data analysis module may be hidden for a predefined period of time, after which they will reappear on the list. This is typically done when support staff is waiting for something to happen with respect to the mobile robot. To make the list less cluttered, the support can hide that particular from view for a predefined period of time.

As a further feature, the data analysis module stores information related to various issues experienced by the mobile robots in a database. This database may be mined by the support staff to generate maps and charts illustrating the frequency of problems a mobile robot or location is experiencing.

In accordance with the present invention, a method of managing and prioritizing for action fleets of mobile robots deployed at various locations is also provided. The method generally includes the steps of receiving, at a homebase server deployed at a particular location, operational parameter data from a plurality of mobile robots operating at the particular location; receiving, at a central server, the operational parameter data for the mobile robots from a plurality of homebase servers, with each homebase server typically deployed at a different location; analyzing, by a data analysis module at the central server, the operational parameter data for the mobile robots; and prioritizing, by the data analysis module, the mobile robots operating at the various locations for action by support staff.

The method further includes the step of displaying, by the data analysis module, a prioritized list to the support staff, the prioritized list ranking the mobile robots in order of importance for action by support staff. The prioritized list may rank the mobile robots based on the severity of the operational and/or navigational issues being experienced. The prioritized list may be accessed by the support staff using a web-based application. In one form, the prioritized list includes links to other information about the mobile robot and the location at which the mobile robot is operating. Additionally, the prioritized list can include operational information about the mobile robot. To assist support staff in identifying issues and addressing them, the operational information may be color coded to identify potential critical issues.

The operational parameter data generally represents operational and navigational issues experienced by the mobile robot. The operational parameter data is processed, by the data analysis module, using a set of business rules. These business rules may be location and mobile robot specific.

As an organizational feature, the mobile robots appearing in the prioritized list may be hidden for a predefined period of time, after which they will reappear on the prioritized list.

The inventive method also includes the step of storing, by the data analysis module, information related to various operational and navigational issues experienced by the mobile robots in a database. The inventive method can further include the steps of analyzing the stored information related to various operational and navigational issues experienced by the mobile robots, and generating maps and/or charts illustrating the frequency of problems a mobile robot or location is experiencing.

In a further embodiment, the home base servers may be omitted. The functionality associated with the home base servers would be included in the central server, which would receive the raw operational data directly from the mobile robots via known or conventional methods and techniques, and process the data to prioritize the mobile robots for action by support staff.

It is an object of the present invention to provide a system and method of managing and prioritizing for action fleets of mobile robots deployed at various locations.

It is a further object of the present invention to provide a prioritized list of mobile robots requiring action to support staff, so that the support staff may quickly and easily determine what issues to address first.

It is an additional object of the present invention to provide data mining capabilities so that issues pertaining to mobile robots and locations may be tracked for analysis and correction of the issues.

Other objects, aspects and advantages of the presently described system and method can be obtained from a study of the specification, the drawings, and the appended claims.

BRIEF DESCRIPTION OF THE DRAWINGS

The inventive system and method is explained hereinafter in more detail by way of example and by means of exemplary embodiments illustrated in the various figures included herewith. In the figures:

FIGS. 5-8 are exemplary screens of web pages generated by the inventive system and method in organizing and prioritizing mobile robots operating at numerous facilities;

FIG. 10 is a chart of color or other coding use to identify particular problems being experienced by a mobile robot;

DETAILED DESCRIPTION OF THE INVENTION

Figure 1:
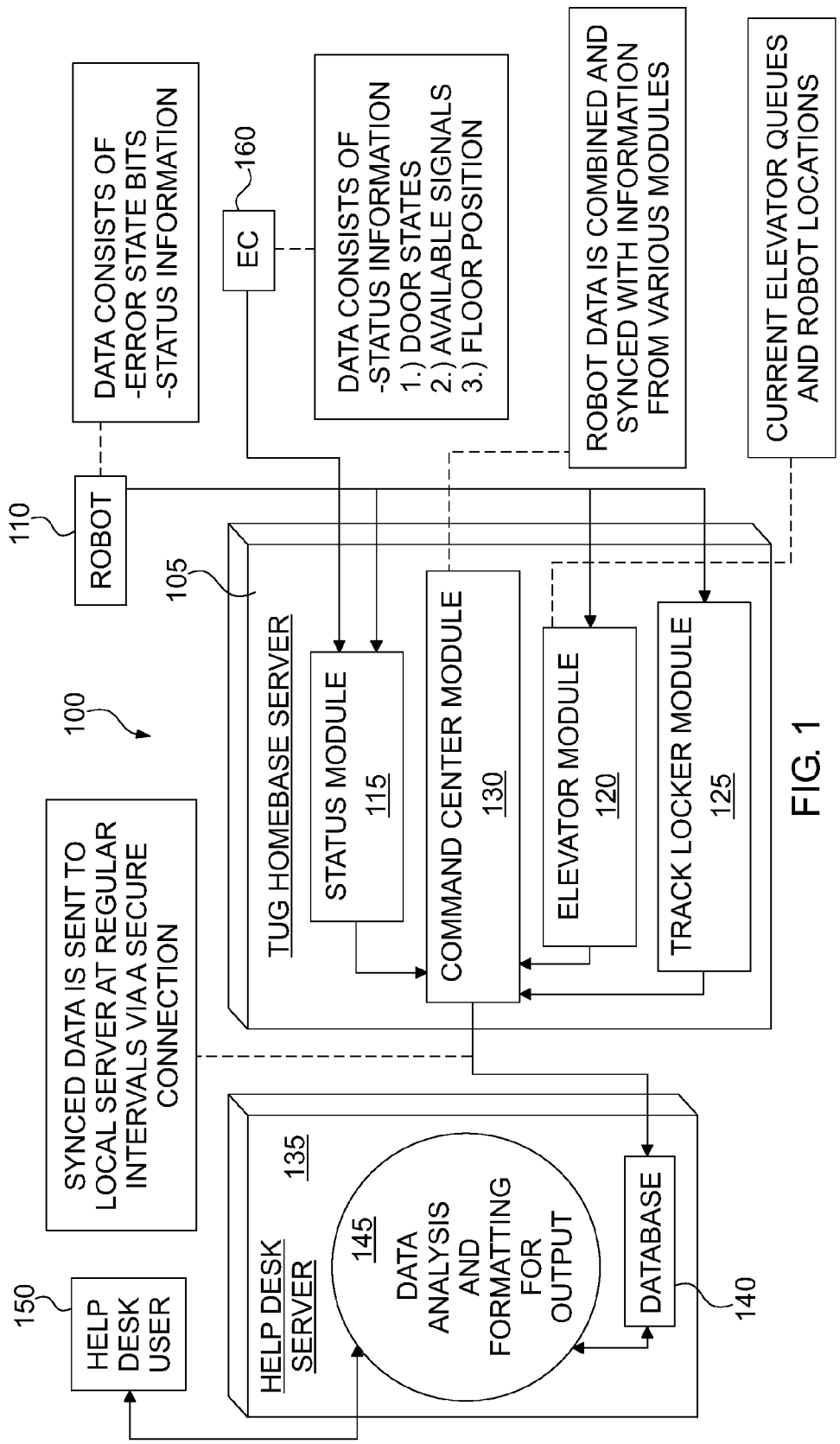
FIG. 1 is a schematic of an exemplary system architecture in accordance with the inventive system and method including one mobile robot.

With many autonomous mobile robots deployed at numerous facilities or locations, a remote monitoring, diagnostic and tracking system is necessary to enable centrally located support personnel, who are remote from the facilities, to efficiently manage their operation. As used herein, the terms "autonomous mobile robot", "mobile robot", "robotic Tug", "robot" and "Tug" are used to mean the same or similar devices. The inventive system and method utilizes heuristic algorithms to analyze operational issues being encountered by a large fleet of mobile robots across multiple facilities. Using these algorithms, the central system determines the most critical navigation issues and rapidly cycles these robots to the "top of the stack" for analysis and support by remotely located support staff. Each mobile robot is equipped with sensors which detect error, status, navigational and other data affecting the mobile robot. Software on each mobile robot monitors and reports key operational parameters and data to a central server located at each facility. The key operational parameters and data are monitored/captured on each mobile robot and transmitted to the central facility server in real time. The technology allows for rapid analysis, display and processing of the real time sensor data from each robot. Additionally, the inventive system can provide a visual display of operational issues including, but not limited to, facility modifications (construction changes), frequency of robot sensor trips (heat maps) and a "Top 10" list of site issues for the support staff.

The inventive system and method includes a multi-user, web-based application ranking and displaying operational parameters for each active robot. A remotely located central server logs and manages data from multiple sites and robots. A web-based application at the central server parses the information and displays it in a useful, ranked form for remote support. The information is displayed to the support in such a manner that they may quickly and easily identify those robots having the most serious navigational issues and address those first.

A key element of this functionality is the use of knowledge-based parameter ranking to optimize robot movement and identify serious navigational issues. Also, a graphical data mining tool assists remote support staff with prioritization and rapid identification of robot navigation issues based on a problem frequency display. Operational issues, sensor readings, performance factors, etc. may be highlighted using heat map display of frequency.

Each facility where the mobile robots are located includes its own homebase server. Each such homebase server includes a software module running thereon which receives operational parameter data from the mobile robots operating at the facility. The software module tracks and funnels pertinent information on each mobile robot. Key operational parameters are then reported by the homebase servers to the remote central server.

Software and sensors are located on each mobile robot that monitor and report key operational parameters to the homebase server at each facility. Each mobile robot, or all mobile robots at a site, can be tuned to provide appropriate levels of information and data for the remote support staff.

The inventive system and method uses a complex algorithm which tracks multiple data points in real-time and ranks mobile robots having issues in order of navigational severity. Navigational severity accounts for, among other things, robot idle time (no motion) caused by facility issue such as, but not limited to, elevator delays, blocked pathways (obstacles in hallway) and failed equipment (automated doors not opening on command). With this information, remotely located support personnel can assist robot navigation, as well as notify facility personnel about issues with their equipment that is affecting the robots. In addition, the inventive system and method logs all mobile robot and other activity in a decision support system for future product improvements. Finally, visual data mining tools can be implemented to rapidly identify patterns in behavioral changes by the mobile robots, thus helping to identify and correct root cause issues.

Many implementations of the inventive system and method may be configured without departing from the spirit and scope of the present invention. For example, no specific operating system is required, and the inventive system/method can run on any operating system supporting TCL, PHP, MySQL, etc. An implementation of the technology for sending data to the homebase server may be written using, for example, a combination of TCL and MySQL. The software parsing and displaying of the data may be written using, for example, a combination of HTML, Javascript, PHP and MySQL. In one implementation, the software parsing and displaying of the data to the help desk personnel only requires hardware capable of running a PHP based webserver. The homebase servers (located at each facility deployed with autonomous mobile robots) may utilize hardware capable of running, for example, SSH, TCL and a MySQL client. Of course, one skilled in the art will recognize that the technology architecture allows for the inventive system to be easily ported to a number of equivalent technology platforms as needed. Additionally, the inventive system utilizes various libraries and plugins, such as, for example, Jquery, mysqltcl and datatables. However, none of these libraries/plugins are essential, and any could be replaced with other technologies to implement the same functionality.

In accordance with the inventive system and method, software typically resides at three locations. (1) On Aethon's web server (Helios) (i.e., the remotely located central server). This is the software parsing and displaying the data to the support staff. (2) On each homebase server at each client or customer location. Each location has one homebase server which all Tugs communicate with and share details of its current situation. This is the software that funnels the status information and data back to the database at the central server. (3) On each mobile robot at a customer location. Each robot runs algorithms to provide raw operational data to the homebase server and thus directly to the central system. The data can be configured or "tuned" for various levels of data depending on the severity of the issue and the impact on the customer's operations.

Figure 2:
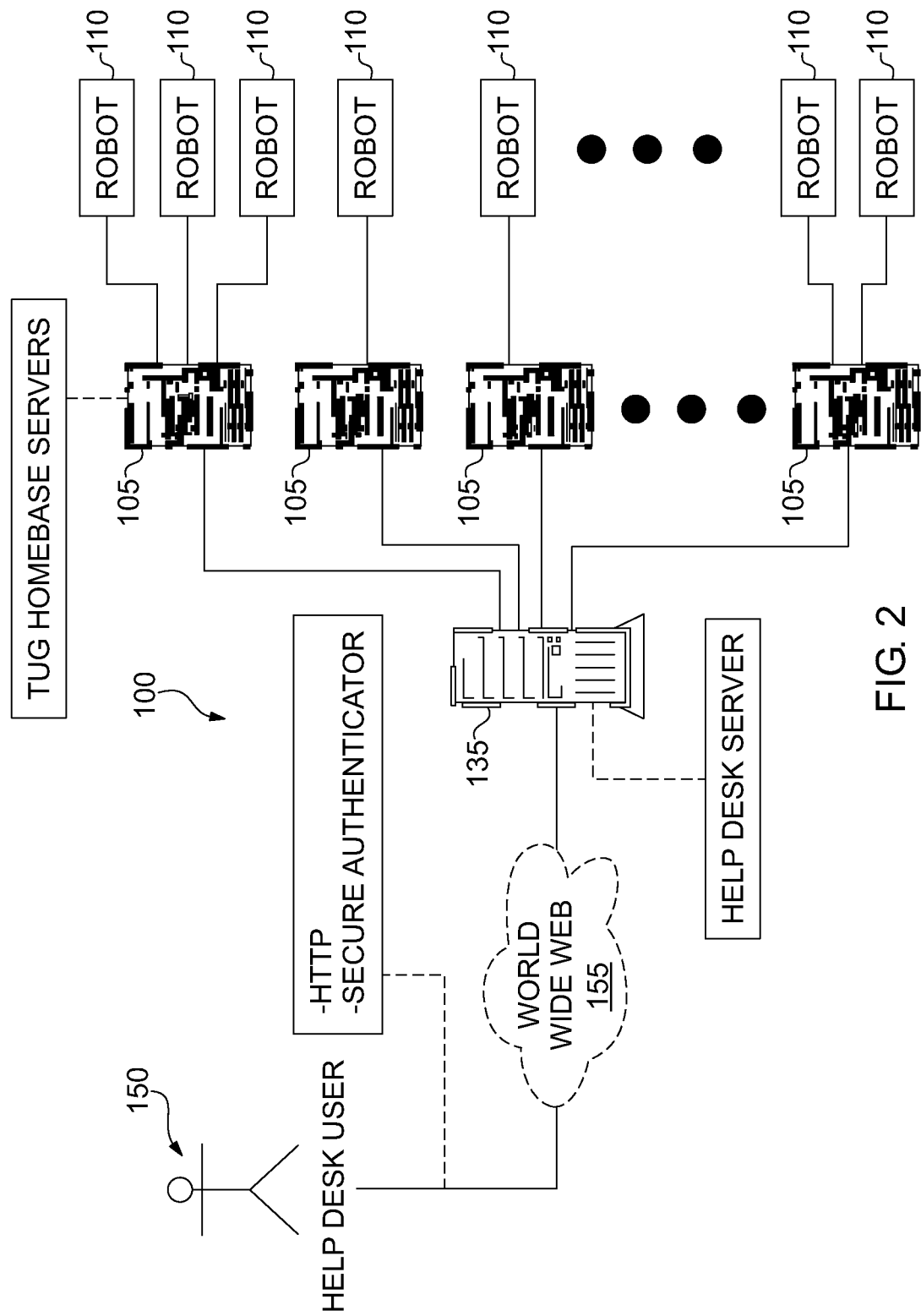
FIG. 2 is a schematic of an exemplary system architecture in accordance with the inventive system and method including a fleet of mobile robots at a plurality of locations.

Referring to FIGS. 1-2, a system for monitoring, diagnosing and tracking autonomous mobile robots is shown generally at 100. The system 100 includes a plurality of homebase servers 105 which receive data from one or more mobile robots 110. Each homebase server 105 is typically situated at a different location and receives data from the fleet of mobile robots 110 deployed at that location. The data received by the homebase server 105 includes error state bits and status information of each mobile robot 110 deployed at the location, which data is monitored by sensors and software provided on the mobile robot 110.

The homebase server 105 includes a status module 115 which receives the data from the mobile robots 110 and the Aethon Elevator Controller (EC) 160. The homebase server 105 also includes an elevator module 120, which receives data from the robot 110 regarding the robot location and queue status, and a track locker module 125 which manages locks and lock queues. The EC 160 (typically one per cabin) receives operational status information of the elevator cabin at the hospital including, for example, cabin position/status and door position/status, and reports the information to the status module 115 at the homebase server 105. A command center module 130 at the homebase server 105 receives data from the status module 115, elevator module 120 and track locker module 125. The command center module 130 synchronizes the data for the site devices, prioritizes the data, and passes the information to the database 140 at the help desk server 135.

The command center module 130 transmits the processed data to a remotely located central server 135. In one form, the data is synced and sent to the central server 135 at regular intervals via a secure connection, such as, for example, a VPN (Virtual Private Network) tunnel and the like. The central server 135 receives data from the various homebase servers 105 located at the various facilities and stores the received data is in a database 140. The central server 135 includes a data analysis module 145 which processes the data from the database 140 using heuristic algorithms to analyze the operational issues being encountered by the mobile robots 110 at the various locations. The data analysis module 145 applies different weights to the various operational parameters depending upon both the operational parameter and the state of the operational parameter in order to rank the various navigational issues being experienced by the mobile robots 110 in order of severity. The various operational parameters analyzed by the data analysis module can include, but are not limited to, idle time, status, itinerary, communication status, whether an alert has been issued (as will be described below), what the Tug is doing, where it is at in its job, what is holding it up, what is producing the idle time, etc., as well as other parameters associated with the mobile robots, including at least those discussed with respect to FIG. 5 below.

The data analysis module 145 utilizes high-level business rules to process the operational parameters and prioritize the Tugs having issues. Some of the business rules may be site specific, Tug specific, job specific, etc. Thus, the business rules may vary not only between sites, but also between Tugs. Some examples of the business rules utilizes by the data analysis module 145 to translate the operational parameters into settings for recovery prioritization include, but are not limited to:

Tug navigation pathways (based on hospital maps).
Pathway properties—e.g., speed, passing ability, etc.
Pathway sensor settings—e.g., which sensors are active at any point.
Sounds messages—e.g., traveling, destinations, elevators, etc.
Destination and locking point wait times.
Lock point and staging area locations.
Elevator interactions—e.g., wait times, Tug transit properties elevator order, backup elevators, etc.
Minimum charging times (typically, charging is not considered "idle time").
Scheduled Tug runs.
Site and Tug prioritization/filtering (typically used for new site "go live" monitoring).

The data analysis module 145 determines the most critical navigation issues and will move those mobile robots 110 experiencing such critical navigation issues to the top of the list for action by support staff 150. The support staff 150 can access the central server 135 using a PC or other computing and display means via the World Wide Web 155 using a web-based application. Alternately, the central server 135 can be situated at the same location as the support staff 150. The central server 135 displays the information to the support staff 150 in a ranked format such that the support staff 150 can quickly and easily determine which mobile robots 110 are experiencing the most critical navigational issues and address those first.

In addition to processing and displaying the navigational information, the data analysis module 145 also stores information related to the various issues each mobile robot 110 is experiencing in the database 140. This stored information may be utilized by the support staff 150 to generate maps and charts illustrating the frequency of problems a mobile robot 110 or location is experiencing.

Figure 3:
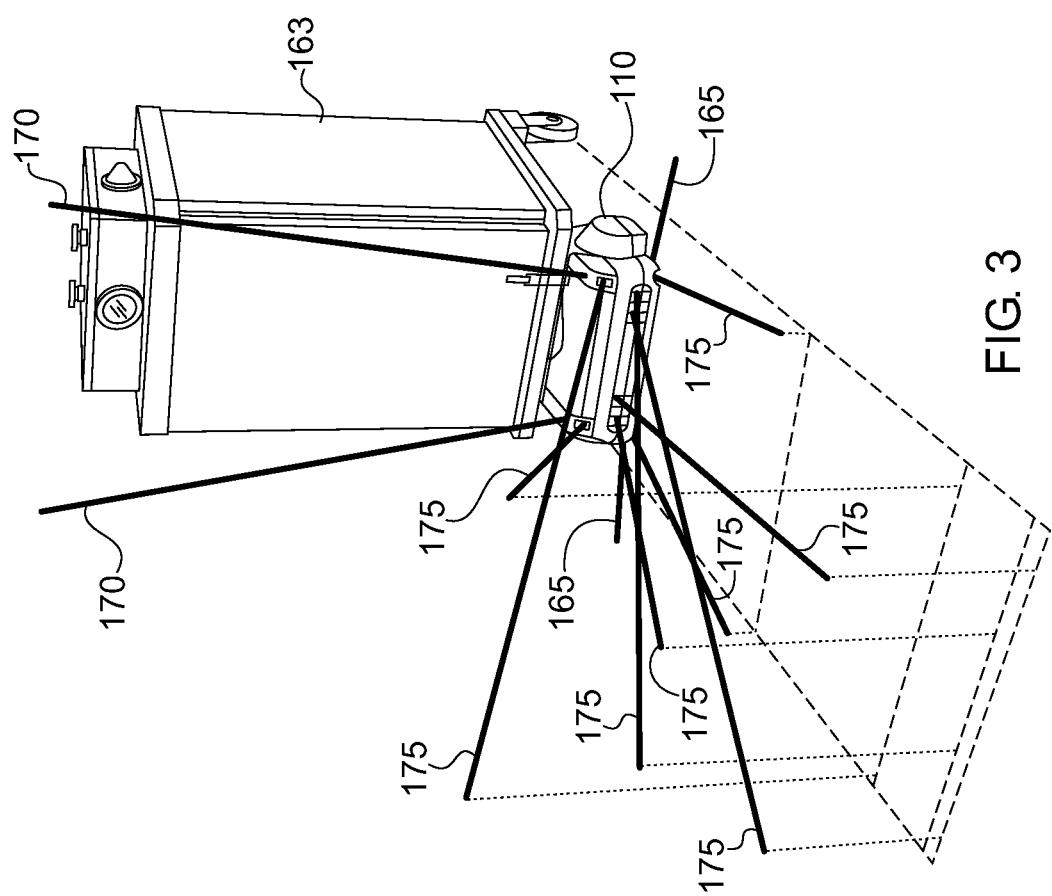
FIG. 3 is an exemplary view of a mobile robot including a plurality of sensors for detecting obstacles.

FIG. 3 illustrates an exemplary mobile robot 110 which may be utilized according to the inventive system and method. The mobile robot 110 includes an attached exemplary cart 163. Of course, mobile robot may be implemented with an integral cart or storage area. FIG. 3 also illustrates an exemplary configuration of sensors that may be implemented to sense potential obstructions. For example, two sensors 165 may be positioned approximately 90-degrees from the direction of movement of the robot 110 and parallel to the floor. These "side" sensors 165 determine the distance to a wall or other object. Two sensors 170 may point almost vertically out of the robot 110, and may be used to detect objects that may hang from the ceiling or protrude from a wall, etc. A variety of different rows of forward facing sensors 175 may be provided which can detect obstacles that are generally in front of the robot 110. The sensors 175 may be grouped in a series of planar rows that are positioned various angles with respect to the floor, and may cross each other if desired. The rows and numbers of sensors should be configured to minimize the amount of potential obstructions that may be able to fit between the sensor beams and thus remain undetected.

Depending upon the particular application and/or location of deployment, the mobile robots 110 may include one or more specifically positioned sensors to detect unique obstacles that may be encountered. Additionally, one or more rear-facing sensors may be provided on the robot 110 or cart 163, as needed. The sensors may be any type of sensor capable of detecting obstacles and may include infrared sensors, ultrasonic sensors (such as sonar), etc. One skilled in the art will appreciate that virtually any configuration and positioning of sensors may be implemented without departing from the spirit and scope of the present invention.

The mobile robot 110 includes an onboard computer (not shown), which is loaded with the robot operating system software. This software utilizes a detailed map of the hospital along with sophisticated navigation and operational software to plan mobile robot routes, avoid obstacles, track its location and provide raw operational data to the homebase server 105 through the use of sensors and other devices.

Figure 4:
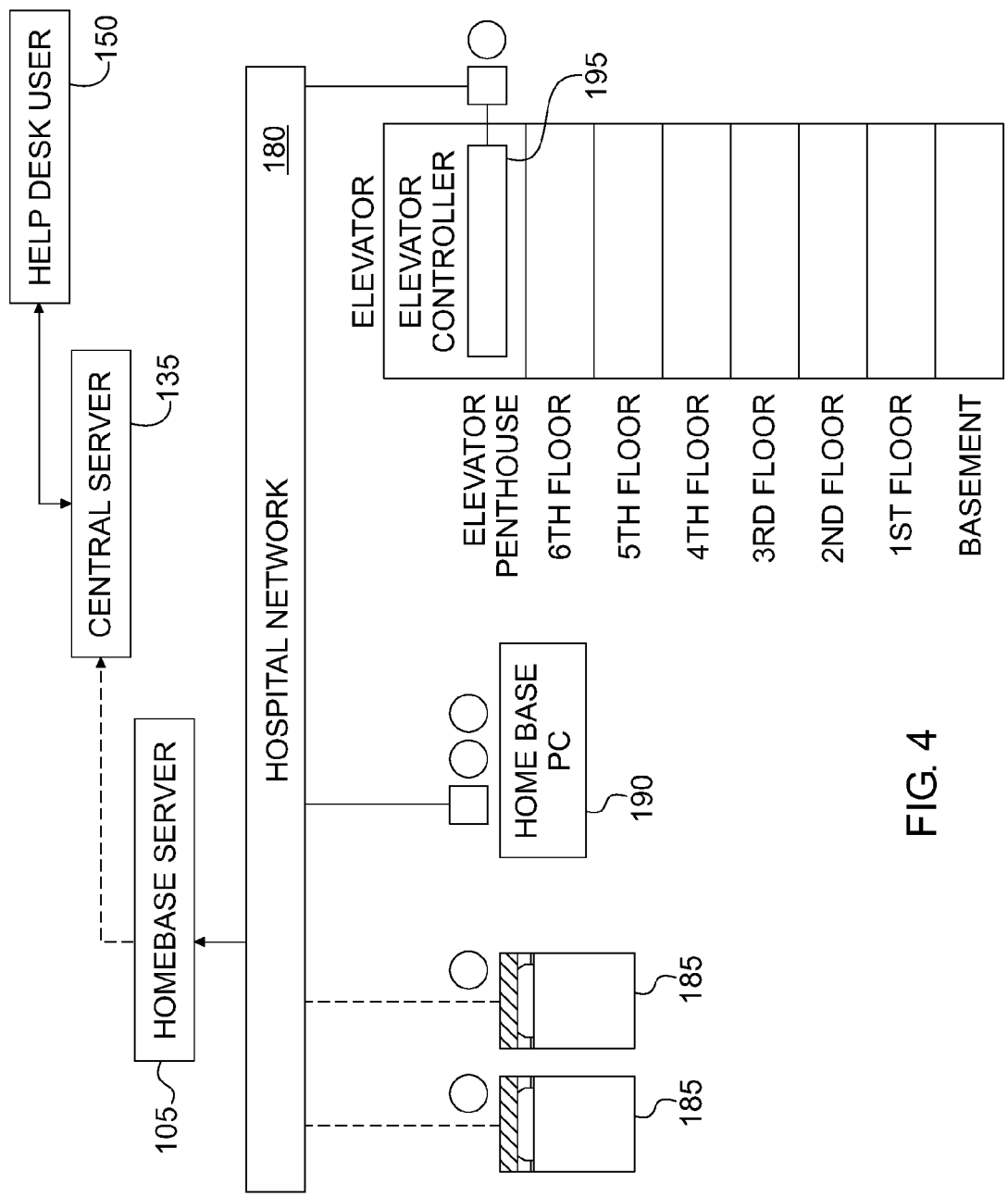
FIG. 4 is a schematic of an exemplary network architecture for use with the inventive system and method.

FIG. 4 illustrates an exemplary network diagram of a hospital for implementation of the inventive system and method. The main communication hub of the network is the existing hospital (or other location) network 180. This can be a wired or wireless Ethernet connection, but one skilled in the art will appreciate that it may take many alternate forms all falling within the spirit and scope of the present invention. Connected to the hospital network 180 are docking stations 185 and a home base computer 190. Mobile robots 110 typically use rechargeable batteries, and the docking stations 185 are used to recharge such batteries. An elevator control 195 is provided which is operatively attached to the hospital robot at one end for communication with the mobile robots 110 and is operatively attached to the elevator control panel on the other end to control the elevators when requested by the mobile robots 110.

The homebase server 105 is connected to the hospital network 180 via a wired or wireless connection. The homebase server 105 receives the raw operational data from the mobile robots 110. The homebase server 105 processes the data and transmits it to the remotely located central server 135. As previously described, the central server 135 processes the data using sophisticated algorithms and displays the information to support staff 150 in a ranked format so that the support staff 150 and efficiently determine while mobile robots 110 are experiencing the most serious navigational issues so that those may be addressed first.

FIG. 5 shows a screen image representing an implementation of the web-application at the central server 135 that is used to organize and prioritize live autonomous mobile robots 110 navigating at numerous facilities. As shown in FIG. 5, the mobile robots 110, which are deployed at various locations, are organized in a list which ranks them in terms of navigational severity. In addition to providing the robots 110 in a list format, various information may be formatted, for example, color coded, depending upon the degree of the issue being encountered. Thus, in addition to the top-to-bottom listing of mobile robots 110, the color coding (or other formatting) provides and additional indication of navigational severity that support staff may use to prioritize which robots 110 to address first.

Various operational parameters are displayed for each active robot 110. For example, at 200, the mobile robot is identified by Tug number and location. The identifier "Tug-120-1" indicates Tug #1 at location "120", and the identifier "Tug-116-4" indicates Tug #4 at location "116". At 205, the status of each Tug is provided. This tells the support staff what the Tug is currently doing. For example, the Tug could be charging, waiting, blocked, navigating, etc. At 210, the battery charge status is provided, which tells the support staff how much battery life is remaining. At 215, the amount of time that has elapsed since the Tug started its last job, or run, is set forth. At 220, the amount of time that the Tug has been idle (not moving) is provided. Typically, this is an important parameter, as an idle Tug is a first sign that the Tug could be experiencing a navigation issue. At 225, the itinerary of the Tug is provided. The itinerary sets forth the list of places (one or more) that the Tug is supposed to go. A check mark, or other indicator, next to the location means that the Tug has completed the run and made it to the destination. For example, Tug "Tug-98-3" near the middle lists "Trauma1" and "WW5S" as its two destinations. Support staff can tell that the Tug reached destination "Trauma1", as there is a check mark next to it, and is currently on its way to "WW5S". At 230, the lock status of the Tug is set forth. The lock status tells the support staff whether the Tug is waiting at a lock, or holding point. Hospitals and other facilities have various locks at various locations. For example, it may be that in a particular hallway, only one Tug can fit at a time. That hallway will have locks at either end. When a Tug reaches that hallway, it waits at the lock if another Tug happens to be navigating through the hallway. Once the hallway is clear, the Tug will proceed down the hallway and other Tugs will be forced to wait at the locks until the hallway is clear. As a further example, a lock could also be located outside an elevator where the Tug will wait for the elevator. At 235, the amount of time that has elapsed since the Tug last communicated with the homebase is provided. This is an important parameter, as all Tugs should be communicating with the homebase system at all times. If a Tug loses communication with the system, it must be determined when, where and why such communication was lost. At 240, the number of outstanding service tickets is provided. This tells the support staff some action has been taken to correct a problem associated with that particular Tug. The service ticket 240 tells the support staff that the Tug has been handed over to the service group and there is a pending service ticket where service personnel are scheduled to go look at the Tug. At 245, the column headed "Past Week" shows the number of recoveries performed by support staff at the area where the Tug is currently experiencing a problem over the past week. By "area" is meant an X-Y-Z coordinate position on the floor plan at the location where the Tug is being deployed. For example, the area could be a 10'×10' location on the floor plan map of the location. However, the physical area could be made bigger or smaller depending on the particular application and/or location. The "Past Week" data is useful to the support staff, as they can see that other Tugs also had problems in the area where the currently Tug is experiencing a problem. Information with respect to problems other Tugs have had in the same area can be useful in figuring out a solution, both short term and long term. At 250, clicking the "C" button allows a support staff member to claim a particular Tug to work on. This helps avoid duplication of work. At 255, the support staff can hide a Tug from the list that the staff knows will not require action for some period of time even though the Tug may be idle. Typically, the Tug must be tied to a service ticket in order for it to be hidden. A reason for the hide is listed in the service ticket. For instance, the reason could be "check back with department regarding reboot" or "check to see if elevator is working", etc. The hide feature has a timer built into it. After the period of time has elapsed, the Tug will appear back on the screen reminding the support staff that action needs to be taken. It will be understood by one skilled in the art that the parameters identified above are exemplary only, and other parameters may be shown and analyzed in ranking the Tugs without departing from the spirit and scope of the present invention.

As discussed previously, the information provided may be color coded or shaded, or otherwise include a visual distinction, to aid support staff in identifying critical issues. The color or visual coding will be dependent on the particular status of a Tug. For example, as shown in FIG. 10, various different colors and/or shading and/or other visual distinctions in listing a Tug may be implemented to identify various critical issues. As shown in FIG. 10, the color legend column 500 include various visual distinctions in listing a Tug that represent a particular status of a Tug as shown immediately to the right in the problem column 505. The chart of FIG. 10 is exemplary only, and more or less colors, shading and/or visual distinctions/coding can be implemented depending on the application and/or location.

For example, if a Tug is waiting at a lock for an elevator or a hallway to clear, rules are set providing a reasonable amount of time that the Tug may have to wait at a particular lock. Similarly, if a Tug is at a destination, rules are set providing a reasonable amount of time that the Tug may have to wait at a particular destination. The reasonable times at each location/destination may differ. The rules take into account the setting of the particular Tug at the particular location or destination in order to apply the color or other coding.

For example, say 5-minutes is set as a reasonable amount of time for a Tug to wait at a particular lock. After 5-minutes has elapsed, the idle time may be color or otherwise coded to indicate an idle time exceeding the typical wait. After 15-minutes, the idle time may be coded to a different color, shading, etc. to indicate a potential critical issue. This color or other coding may continue in time increments indicating the continued severity of the wait. Of course, the other parameters shown in FIG. 5 may also be color or otherwise coded dependent upon the parameter or a combination of parameters.

The inventive system and method applies different weights to the various parameters depending upon the parameter, its state, as well as the other parameters and their states, all in relation to the particular Tug. Business rules are utilized that involve what the Tug is doing, where it is in its job, what is holding it up, what is producing the idle time, and various conditions of those and other parameters that create the prioritization list shown in FIG. 5. Colors are associated with various parameters to flag not only prioritization on the list, but also the relative area(s) where the problem may be occurring.

For example, Tug "Tug-120-1" appears first on the list of FIG. 5. It shows that it is charging on the second floor (205), started its last job approximately 41 minutes ago (215), has been idle for over 15 hours (220), has no itinerary (225), has been out of communication for over 19 hours (235), and has 1 service ticket (240). Additionally, one other Tug has experienced a problem in the area in which Tug-120-1 is currently experiencing a problem, as evidenced by the 1 in the Past Week column (245). The job start and idle time data are non-sensical, and because the Tug has been out of communication for almost 20 hours, all of the other data is suspect. Based on a combination of these factors, Tug "Tug-120-1" is placed at the top of the list. The other Tugs in the list are similarly ranked based on a combination of the various parameters. Thus, support staff does not have to figure out which Tug should be addressed first.

Figure 12:
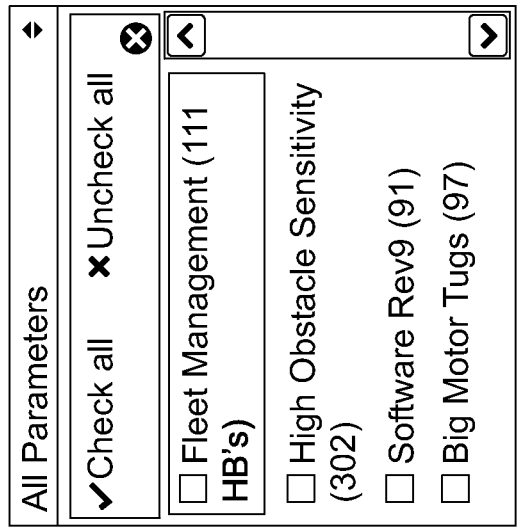
FIG. 12 illustrates a dropdown list used for filtering Tug selection by various Parameters that have been preset in the inventive system.
Figure 11:
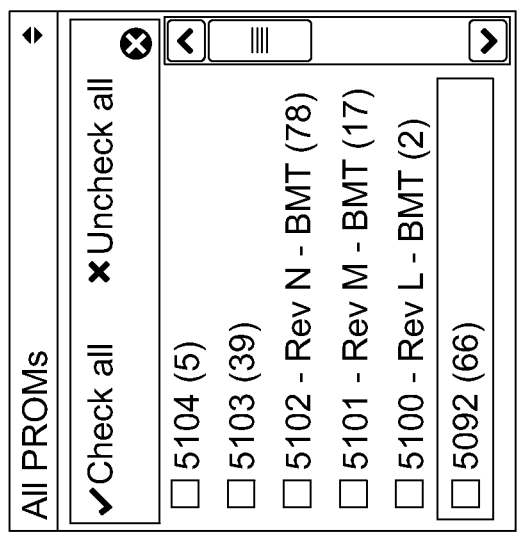
FIG. 11 illustrates a dropdown list used for filtering Tug selection by Firmware Version—e.g., used on the Tug.

Additionally, the list of Tugs to be reviewed can be filtered by Site # (e.g., "All Sites"), Software Version (e.g., "All MNZ Versions"), Firmware Version—e.g., on the robot (e.g., "All PROMs"), and any newly implemented code modules (e.g., "All Parameters"). These filters are a useful tool for both support personnel and development staff for reviewing issues across the fleet(s) of Tugs or monitoring newly developed functionality. For example, clicking the button 510 on FIG. 5 may display a dropdown list of Firmware Versions currently running on the Tugs, as shown in FIG. 11. A user can check some or all of the currently running Firmware Versions to be displayed on the exemplary screen of FIG. 5. Similarly, clicking the button 515 on FIG. 5 may display a dropdown list of various parameters that have been identified for monitoring, as shown in FIG. 12. A user can check some or all of the parameters to be displayed on the exemplary screen of FIG. 5. Similarly, clicking the button 520 on FIG. 5 may display a dropdown list (not shown) of the various sites that have operating Tugs. A user can check some or all of the sites to be displayed on the exemplary screen of FIG. 5. By checking various combinations of sites, PROM Versions, and Parameters, the support staff can implement various filtering options and checkbox functionality.

Figure 6:
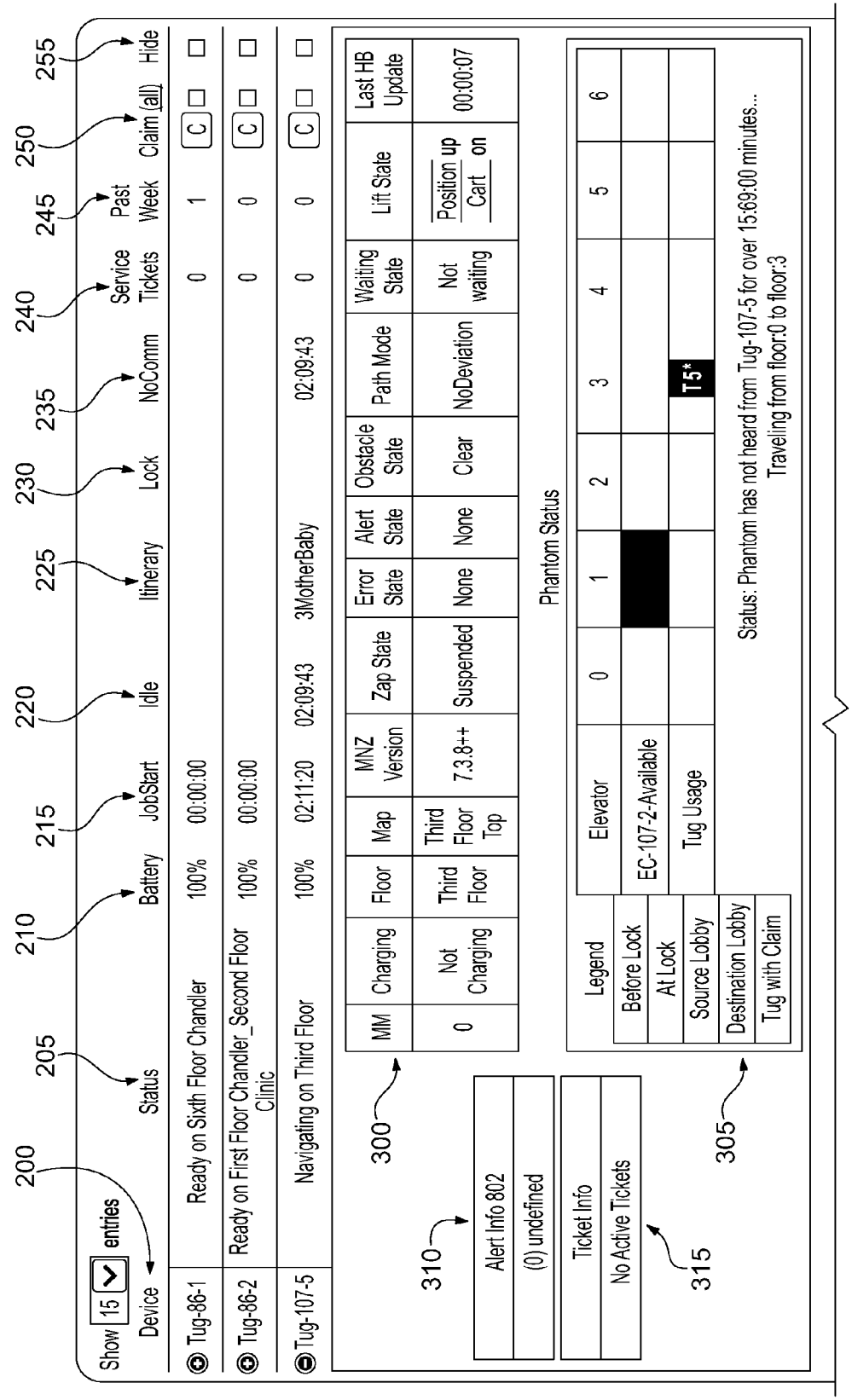

FIG. 6 shows a screen image providing additional support data to the remote support staff 150. By clicking the "+" sign next to the Tug identifier 200, the support staff is provided with additional information about the Tug, including its navigation state, hardware properties, etc., as well as facility information that assists the support staff in solving any issues the Tug may be having. For example, Tug "Tug-107-5" indicates idle and no communication times of over 2 hours, which may be a reason for accessing it. The table shown at 300 provides various operational parameters of the Tug for the support staff. "MM" tells the support whether the Tug is in maintenance mode, meaning the Tug is being serviced by service personnel. In maintenance mode, the Tug is unable to go out. A "0" means no, and a "1" means yes. As an example, the Tug identifiers 200 for Tugs "Tug-86-1" and "Tug-86-2" are shaded, which is an indication to the support staff that they are in maintenance mode. Thus, even though they are at the top of the list, the support staff knows they are being serviced and can move to the next Tug.

In Table 300, "Charging" indicates whether the Tug is charging or not. The "Floor" and "Map" parameters indicate what floor and section of the floor the Tug is on. "MNZ Version" tells what version of the software is running on the Tug, and "Zap State" indicates the Tug's state of processing the software. "Error State" and "Alert State" are related and provide an indication of software errors. "Obstacle State" tells whether the Tug is detecting any obstacles. "Path mode" indicates the travel mode of the Tug. For example, the Tug may be on a deviation travel mode where the Tug can maneuver around obstacles, or a no deviation travel mode where the Tug cannot maneuver around obstacles. "Waiting State" tells whether the Tug is waiting at a lock. "Lift State" tells whether a cart is attached to the Tug. "Last HB Upgrade" tells when the last communication with the homebase occurred. Thus, viewing FIG. 6, the support staff can ascertain that Tug "Tug-107-5" is destined to go to location "3MotherBaby" and has been idle for over 2 hours, but has communicated with the home base 7 seconds ago. This indicates that the system is functioning normally and there is a problem with the Tug.

Table 305 in FIG. 6 provides information about the elevators the Tug is using. Table 305 is typically color or otherwise coded to indicate where the Tug is in the elevator process. Table 305 tells the support staff that the Tug "Tug-107-5" was supposed to go to from floor 1 to floor 3 and it got off the elevator on floor 3. This provides a clue to the support staff as to where the Tug was the last time it was heard from. Table 305 further indicates that the elevator "EC-107-2" is on the first floor.

Table 310 provides alert information in the event of an alert. An alert is generated by a Tug when it experiences a problem. The alert summarizes the Tug's overall status and may provide an indication of what the Tug thinks is wrong. The alert tells the support staff that there is other information to look at which has been generated by the Tug that may be useful in solving the problem the Tug is experiencing. Support staff would click on the alert link provided in the table to view information regarding the alert. Similarly, table 315 provides service information in the event of a service ticket being opened. Support staff would click on the service ticket link provided in the table to view information regarding the alert. As shown in table 315, Tug "Tug-107-5" has no alerts or opened service tickets.

Figure 7:
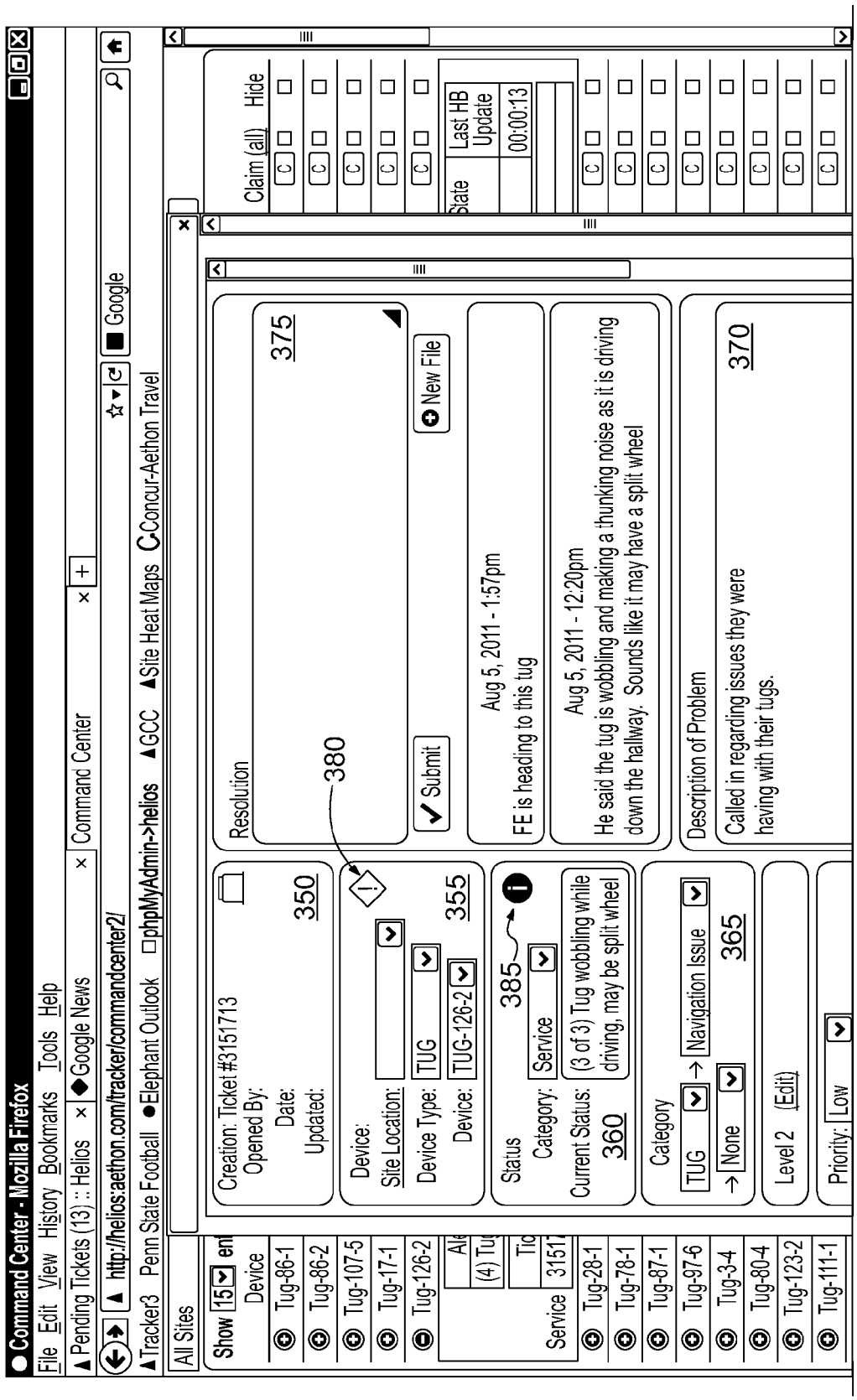

FIG. 7 shows an image of the inventive system linked into a customer support database allowing issues to be documented in a support ticket. This screen can be accessed by clicking the service ticket link in table 315 (see FIG. 6). The screen shot of FIG. 7 provides support staff with information related to an open service ticket. Box 350 identifies the ticket number, who opened the service ticket, the date it was opened, and the date(s) it was updated. Box 355 identifies the site location, the device type and device number of the Tug being serviced. Box 360 identifies the category of service being performed and the current status of the service. Box 365 and boxes below it provide further information to the support staff regarding the particular service ticket. Box 370 provides a description of the problem being experienced by the Tug. Box 375 is a resolution box for support staff to type in entries. Each time there is an update, support staff will input a new entry describing the update. Hitting the "submit" button will add the entry to the list of entries below the resolution box 375, typically in the order of most current on top.

Additional information may be provided to the support staff by clicking on the various icons appearing in FIG. 7. For example, clicking the icon shown at 380 will show any other tickets that are open at the particular site. There may be other Tugs that are having problems, other devices like an elevator may have a ticket open, or the homebase may be having some problems. Clicking on the icon 380 will provide the support staff with additional information about what might be happening at the particular location. Clicking on the icon shown at 385 will show an exploded window which lists any status changes and the reasons for the changes. This again provides the support staff with additional information regarding what has been taking place with the particular situation. All of the information is designed to assist the support staff in solving the problem.

Figure 8:
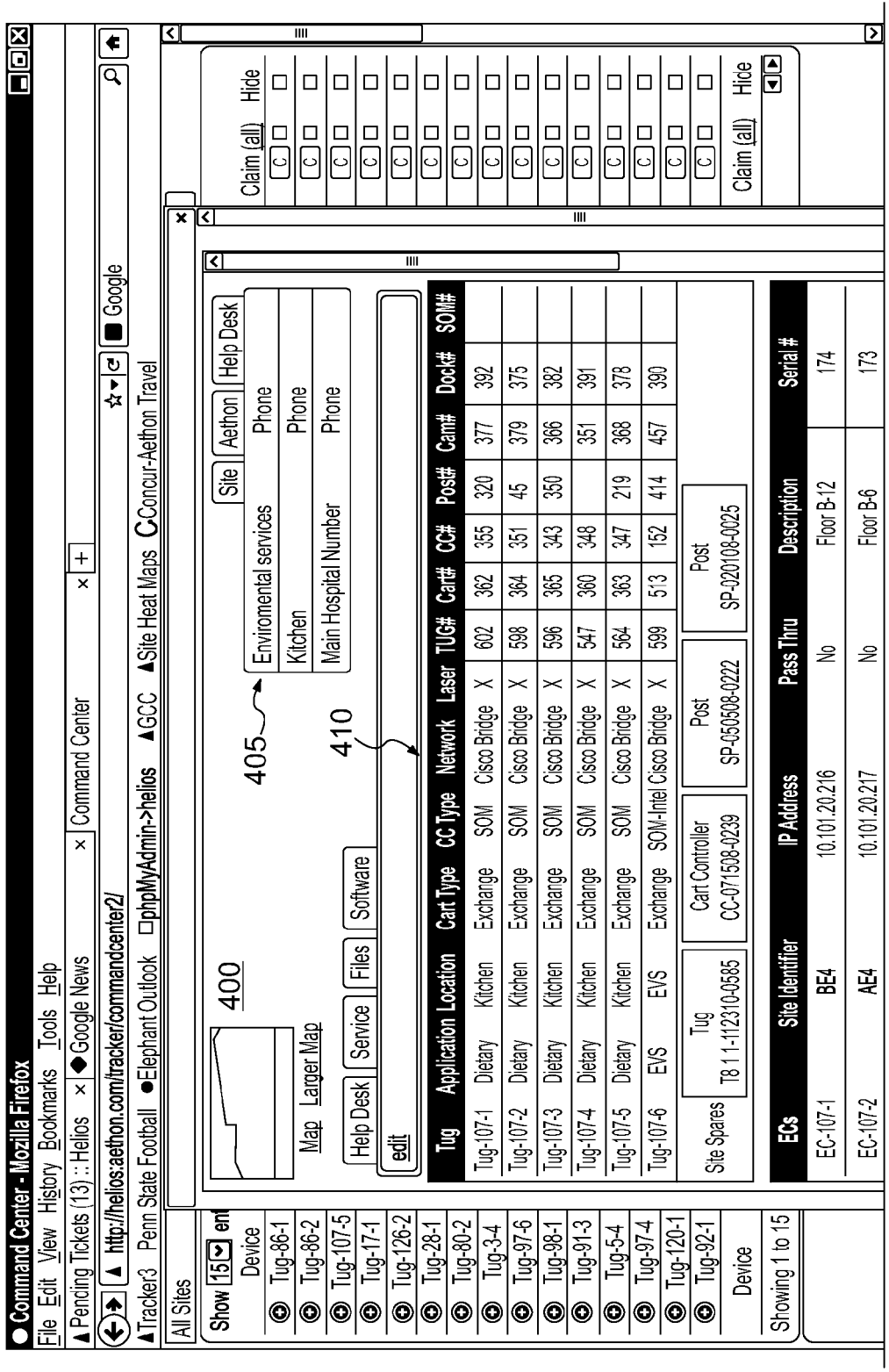

Existing site information can also be displayed to assist support personnel, as shown in FIG. 8. This screen can be accessed by clicking the device name in FIG. 5. For example, this particular screen would have been accessed by clicking the device name "Tug-107-5" in the window behind it. Clicking that link will bring up all information about location 107.

At 400, the site name and address will be provided. Table 405 has various tabs. The "Help Desk" tab, which is shown, identifies who the help desk (i.e., support staff) is supposed to call if they need assistance with an issue. Clicking on the "Site" tab will provide a list of individuals at the site who are supposed to be contacted for various issues. Clicking the "Aethon" tab will provide a list of Aethon support personnel for the particular site.

Table 410 provides various information for each Tug at the particular site. "Tug" provides the Tug identifier number. "Application" identifies the particular application of the Tug. "Location" identifies the location of the charging dock for the Tug. "Cart Type" identifies whether the Tug pulls a cart or not. "CC Type" refers to the type of processor used by the Tug's computer. "Network" identifies the type of network used. "Laser" identifies the presence or absence of a laser sensor. The remaining columns identify inventory numbers for the Tug and the various components and equipment associated with the Tug. The "Site Spares" row below the columns is for the service department and identifies the hardware and equipment that is available at the site that may be used as replacement parts for the Tugs.

Below table 410 is another table providing information concerning the elevators at the particular site. As the support staff scrolls down, further information concerning the particular site can be viewed.

Figure 9:
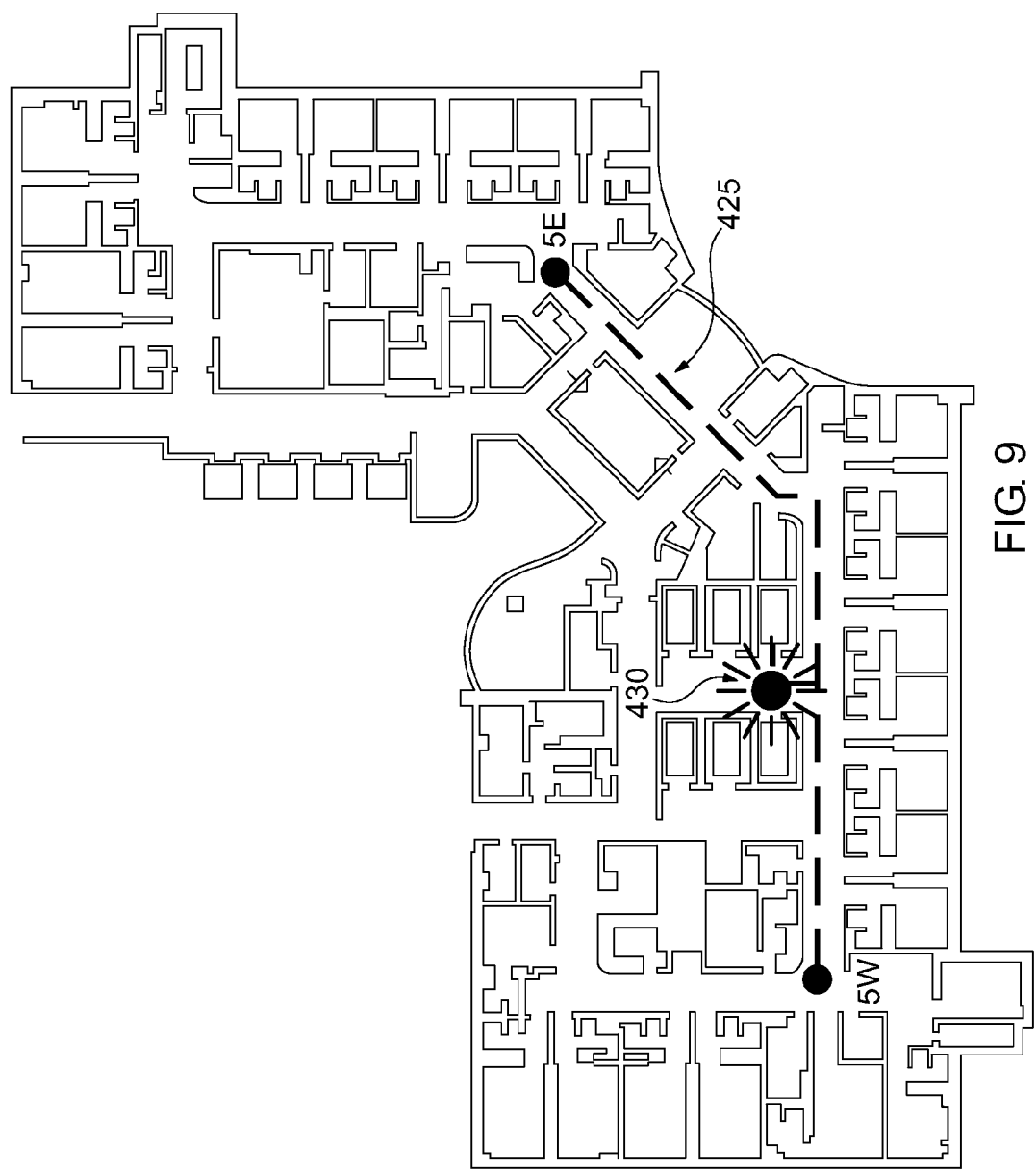
FIG. 9 is a heat map illustrating the frequency of navigational issues experienced by a mobile robot.

FIG. 9 illustrates an example of the data mining functionality using a "heat map" tool to display robot navigation issues at a facility. FIG. 9 represents the 5th floor of a particular facility. As shown in FIG. 9, the particular Tug travels between destinations "5W" and "5E" along the route shown at 425. As shown in FIG. 9, the Tug also accesses the elevators to travel to different floors. As the heat map image shows, the Tug is having particular issues in the elevator lobby on this particular floor, shown generally at 430. Aethon support personnel can use this information to take action to correct the issue. They can contact the client and request onsite assistance to help correct the issue. Alternatively, the support staff can work with the customer to make a mapping change to the robot's instructions allowing it to travel through other hallways to avoid the problem in the future.

It will be understood by one of ordinary skill in that art that while the presently described system and method has been described herein as including home base servers 105 located at each facility where fleets of mobile robots are deployed, the home base servers 105 may be omitted without departing from the spirit and scope of the present invention. In this embodiment, the functionality associated with the home base servers 105 would be included in the central server 135. The mobile robots 110 located at each facility would transmit the raw operational data directly to the central server 135 via known or conventional methods and techniques, and the central server 135 would process the data in a manner as previously described to prioritize the mobile robots for action by support staff.

It will be appreciated that one or more exemplary embodiments of the present invention can employ hardware and/or software aspects. Software includes, but is not limited to, firmware, resident software, microcode, etc., that has been compiled to program a general purpose computer to be a specific purpose computer, or run a specific purpose computer. The memory devices could be implemented as an electrical, magnetic or optical memory, or any combination of these or other types of storage devices (including memory portions as described above with respect to cards). It should be noted that if distributed processors are employed, each distributed processor that makes up a processor carrying out a function or step generally contains its own addressable memory space. It should also be noted that some or all of computer systems and servers can be incorporated into an application-specific or general-use integrated circuit. For example, one or more method steps could be implemented in hardware in an ASIC rather than using firmware. Displays used in conjunction with each of the entities, servers and processors are representative of a variety of possible input/output devices.

Accordingly, it will be appreciated that one or more embodiments of the present disclosure can include a computer program comprising computer program code means adapted to perform one or all of the steps of any methods or claims set forth herein when such program is run on a computer, and that such program may be embodied on a computer readable medium. Further, one or more embodiments of the present disclosure can include a computer comprising code adapted to cause the computer to carry out one or more steps of methods or claims set forth herein, together with one or more apparatus elements or features as depicted and described herein.

Figure 13:
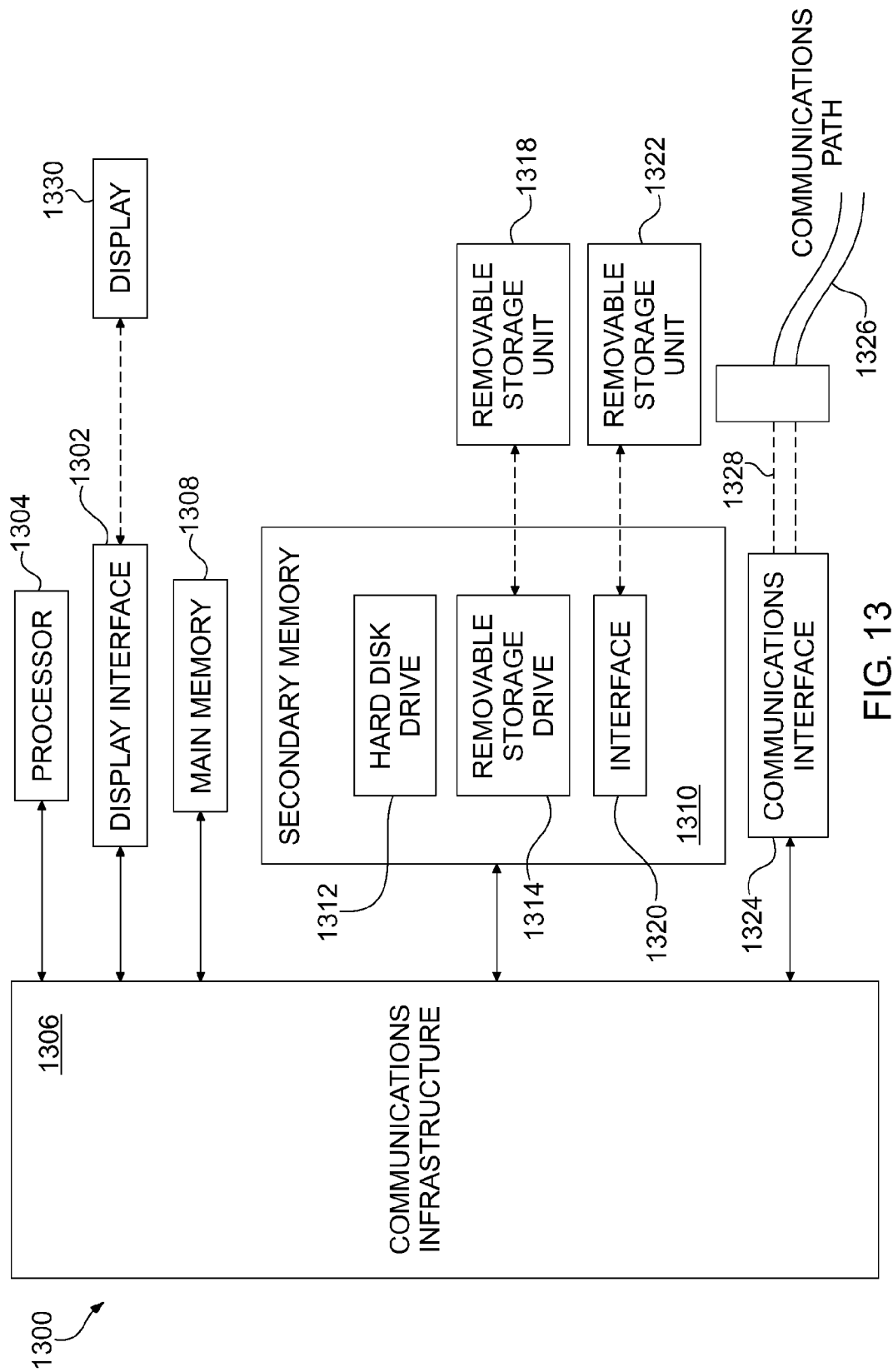
FIG. 13 depicts an exemplary computer system in which embodiments of the present disclosure may be implemented.

As is known in the art, and is described with respect to FIG. 13, all or part of one or more aspects of the methods and apparatus discussed herein may be distributed as an article of manufacture that itself comprises a computer-readable medium having computer-readable code means embodied thereon. The computer-readable program code means is operable, in conjunction with a computer system, to carry out all or some of the steps to perform the methods or create the apparatuses discussed herein. The computer-readable medium may be a recordable medium, for example, floppy disks, hard drives, compact disks, EEPROMs, memory cards, etc. Any tangible medium known or developed that can store information suitable for use with a computer system may be used. The computer-readable code means can be any mechanism for allowing a computer to read instructions and data, such as, for example, magnetic variations on a magnetic media or optical characteristic variations on the surface of a compact disk. The computer-readable medium can be distributed on multiple physical devices (or over multiple networks). For example, one device could be a physical memory media associated with a terminal and another device could be a physical memory media associated with a processing center.

The computer systems and servers described herein each contain a memory that will configure associated processors to implement the methods, steps, and functions disclosed herein. The memories could be distributed or local and the processors could be distributed or singular. The memories could be implemented as an electrical, magnetic or optical memory, or any combination of these or other types of storage devices. Moreover, the term "memory" should be construed broadly enough to encompass any information able to be read from or written to an address in the addressable space accessed by an associated processor.

Although exemplary embodiments have been described herein in terms of a method or system/apparatus, it is contemplated that it may be implemented by microprocessors of a computer, such as, for example, the computer system 1300 illustrated in FIG. 13. In various embodiments, one or more of the functions of the various components may be implemented in software that controls a computing device, such as computer system 1300, which is described below with reference to FIG. 13. The processor(s) of the computer system 1300 are configured to execute the software recorded on a non-transitory computer-readable recording medium, such as, for example, a hard disk drive, ROM, flash memory, optical memory, or any other type of non-volatile memory.

Aspects of the present disclosure shown in FIGS. 1-12, or any part(s) or function(s) thereof, may be implemented using, for example, hardware, software modules, firmware, tangible computer readable media having instructions stored thereon, or a combination thereof and may be implemented in one or more computer systems or other processing systems. FIG. 13 illustrates an exemplary computer system 1300 in which embodiments of the present disclosure, or portions thereof, may be implemented as computer-readable code. For example, the inventive system and method can be implemented in the computer system 1300 using hardware, software, firmware, non-transitory computer readable media having instructions stored thereon, or a combination thereof, and may be implemented in one or more computer systems or other processing systems. Hardware, software, or any combination of such may embody any of the modules and components used to implement the system, method and architecture of FIGS. 1-12.

If programmable logic is used, such logic may execute on a commercially available processing platform or a special purpose device. One of ordinary skill in the art will appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device. For instance, at least one processor device and a memory may be used to implement the above described embodiments. A processor device may be a single processor, a plurality of processors, or combinations thereof. The processor devices may have one or more processor "cores", as that term is commonly understood.

Various embodiments of the present disclosure are described in terms of the exemplary computer system 1300, shown in FIG. 13. After reading this description, it will become apparent to a person skilled in the relevant art how to implement the present disclosure using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

The computer system 1300 includes a display 1330 operable by a user via conventional means that is connected to a communications infrastructure 1306 via a display interface 1302 and controlled via a processor device 1304. The processor device 1304 may be a special purpose or a general-purpose processor device. As will be appreciated by persons skilled in the relevant art, the processor device 1304 may also be a single processor in a multi-core/multiprocessor system, such system operating alone, or in a cluster of computing devices operating in a cluster or server farm. The processor device 1304 is connected to the communication infrastructure 1306 which may be, for example, a bus, message queue, network, or multi-core message-passing scheme. The computer system 1300 also includes a main memory 1308, for example, random access memory (RAM), and may also include a secondary memory 1310. The secondary memory 1310 may include, for example, a hard disk drive 1312, removable storage drive 1314, etc. The removable storage drive 1314 may comprise, for example, a floppy disk drive, a magnetic tape drive, an optical disk drive, a flash memory, or the like.

The removable storage drive 1314 reads from and/or writes to a removable storage unit 1318 in a well-known manner. The removable storage unit 1318 may comprise, for example, a floppy disk, magnetic tape, optical disk, etc. which is read by and written to by removable storage drive 1314. As will be appreciated by persons skilled in the relevant art, the removable storage unit 1318 includes a non-transitory computer usable storage medium having stored therein computer software and/or data.

In alternative implementations, the secondary memory 1310 may include other similar means for allowing computer programs or other instructions to be loaded into computer system 400. Such means may include, for example, an interface 1320 and a removable storage unit 1322 connected thereto. Examples of such means may include, for example, a program cartridge and cartridge interface (such as that found in video game devices), a removable memory chip (such as an EPROM, or PROM) and associated socket, and other removable storage units 1322 and interfaces 1320 which allow software and data to be transferred from the removable storage unit 1322 to computer system 1300. The computer system 1300 may also include a communications interface 1324.

The communications interface 1324 allows software and data to be transferred between computer system 1300 and external devices. The communications interface 1324 may include, for example, a modem, a network interface (such as an Ethernet card), a communications port, a PCMCIA slot and card, or the like. Software and data transferred via communications interface 1324 may be in the form of signals, which may be electronic, electromagnetic, optical, or other signals capable of being received by communications interface 1324. These signals may be provided to communications interface 1324 via an internal connection 1328 and a communications path 1326. The communications path 1326 carries signals and may be implemented using wire or cable, fiber optics, a phone line, a cellular phone link, an RF link or other communications channels.

In this application, the terms "computer program medium", "non-transitory computer readable medium", and "computer usable medium" are used to generally refer to media such as, for example, the removable storage unit 1318, removable storage unit 1322, and a hard disk installed in hard disk drive 1312. Signals carried over the communications path 1326 can also embody the logic described herein. "Computer program medium" and "computer usable medium" can also refer to memories, such as the main memory 1308 and the secondary memory 1310, which can be memory semiconductors (e.g., DRAMs, etc.). These computer program products are means for providing software to computer system 1300.

Computer programs (also called computer control logic) are stored in the main memory 1308 and/or the secondary memory 1310. Computer programs may also be received via the communications interface 1324. Such computer programs, when executed, enable the computer system 1300 to implement the present disclosure as discussed herein. In particular, the computer programs, when executed, enable the processor device 1304 to implement the processes of the present disclosure. Accordingly, such computer programs represent controllers of the computer system 1300. Where the present disclosure is implemented using software, the software may be stored in a computer program product and loaded into computer system 1300 using removable storage drive 1314, interface 1320, and hard disk drive 1312, or communications interface 1324. Embodiments of the present disclosure also may be directed to computer program products comprising software stored on any computer useable medium. Such software, when executed in one or more data processing device, causes a data processing device(s) to operate as described herein. Embodiments of the present disclosure employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.), and communication mediums (e.g., wired and wireless communications networks, local area networks, wide area networks, intranets, etc.).

Accordingly, it will be appreciated by one of ordinary skill in the art that one or more embodiments of the present invention can include a computer program comprising computer program code means adapted to perform one or all of the steps of any methods or claims set forth herein when such program is run on a computer, and that such program may be embodied on a computer-readable medium. Further, one or more embodiments of the present invention can include a computer comprising code adapted to cause the computer to carry out one or more steps of methods or claims set forth herein, together with one or more apparatus elements or features as depicted and described herein.

It is to be appreciated that the Detailed Description section, and not just the Summary and Abstract sections, is intended to be used to interpret the claims. The Summary and Abstract sections may set forth one or more, but not all, exemplary embodiments of the present disclosure as contemplated by the inventor(s) and, thus, are not intended to limit the present disclosure and the appended claims in any way. Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the present disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The breadth and scope of the present disclosure should not be limited by any of the above-described exemplary embodiments, but should be defined only in accordance with the following claims and their equivalents.

While the present invention has described herein with particular reference to the drawings, it should be understood that various modifications could be made without departing from the spirit and scope of the present invention. Those skilled in the art will appreciate that various other modifications and alterations could be developed in light of the overall teachings of the disclosure. The presently preferred embodiments described herein are meant to be illustrative only and not limiting as to the scope of the invention which is to be given the full breadth of the appended claims and any and all equivalents thereof.

We claim:

1. A system for managing and prioritizing for action fleets of mobile robots deployed at various locations, the system comprising:
   a plurality of homebase servers, each corresponding to a different location, wherein each of the homebase servers receives operational parameter data from a plurality of mobile robots operating at a particular location; and
   a central server receiving the operational parameter data from the plurality of homebase servers, the central server including a data analysis module processing the operational parameter data and prioritizing the mobile robots operating at the various locations based on the operational parameter data of each mobile robot using a set of business rules that are location and mobile robot specific; and
   wherein the operational parameter data comprises information regarding operational and navigational issues experienced by the mobile robot; and
   wherein each of the mobile robots are prioritized relative to each of the other mobile robots at the various locations based on a severity of operational and navigational issues experienced by each of the mobile robots;
   wherein the data analysis module provides a prioritized list that ranks the mobile robots in order of severity based on the operational parameter data to a display associated with the data analysis module.

2. The system of claim 1, wherein the information regarding navigational issues comprises information regarding robot idle time caused by elevator delays, blocked pathways, and/or failed facility equipment.

3. The system of claim 1, wherein the central server receives operational status information of an elevator cabin.

4. The system of claim 3, wherein the operational status information of the elevator cabin comprises at least one of a cabin position, a cabin status, a door position, and a door status.

5. The system of claim 1, wherein the data analysis module generates the list prioritizing the mobile robots based on the operational parameter data and ranking them in order of importance for action by support staff.

6. The system of claim 5, wherein the list generated by the data analysis module is accessible using a web-based application, and wherein the list includes links to other information about the mobile robot and the location at which the mobile robot is operating.

7. The system of claim 5, wherein the list generated by the data analysis module includes operational information about the mobile robot, wherein the operational information comprises at least one of idle time of the mobile robot, status of the mobile robot, itinerary of the mobile robot, communication status of the mobile robot, whether an alert has been issued, a task of the mobile robot, where the mobile robot is at in its task, a cause of delay of the mobile robot, and a cause of idle time of the mobile robot, and wherein the operational information is coded to identify potential critical issues.

8. The system of claim 5, wherein data relative to the mobile robots appearing in the list generated by the data analysis module may be hidden for a predefined period of time, after which the data relative to the mobile robots will reappear on the list.

9. The system of claim 1, wherein the data analysis module stores information related to the operational and navigational issues experienced by the mobile robots in a database.

10. The system of claim 9, wherein the data analysis module uses the stored information related to the operational and navigational issues experienced by the mobile robots to generate maps and charts illustrating the frequency of problems a mobile robot or location is experiencing.

11. A method of managing and prioritizing for action fleets of mobile robots deployed at various locations, the method comprising the steps of:
   receiving, at a homebase server deployed at a particular location, operational parameter data from a plurality of mobile robots operating at the particular location;
   receiving, at a central server, the operational parameter data for the mobile robots from a plurality of homebase servers, each homebase server deployed at a different location;
   analyzing, by a data analysis module at the central server, the operational parameter data for the mobile robots;
   processing, by the data analysis module, the operational parameter data for the mobile robots using a set of business rules; and
   prioritizing, by the data analysis module at the central server, the mobile robots operating at the various locations based on the operational parameter data and the set of business rules,
   wherein the operational parameter data comprises information regarding the operational and navigational issues experienced by each of the mobile robots,
   wherein the data analysis module prioritizing the mobile robots operating at the various locations comprises prioritizing each of the mobile robots relative to each of the other mobile robots at the various locations based on a severity of the operational and navigational issues experienced by each of the mobile robots; and
   wherein the business rules are location and mobile robot specific.

12. The method of claim 11, further comprising the step of displaying, by a display associated with the data analysis module, a prioritized list, wherein the prioritized list ranking the mobile robots in order of severity for action by support staff.

13. The method of claim 12, wherein the prioritized list is accessible using a web-based application, and wherein the prioritized list includes links to other information about the mobile robot and the location at which the mobile robot is operating.

14. The method of claim 12, wherein the prioritized list includes operational information about the mobile robot, and wherein the operational information is coded to identify potential critical issues.

15. The method of claim 12, wherein data relative to the mobile robots appearing in the prioritized list may be hidden for a predefined period of time, after which the data relative to the mobile robots will reappear on the prioritized list.

16. The method of claim 11, further comprising the step of storing, by the data analysis module, information related to the operational and navigational issues experienced by the mobile robots in a database.

17. The method of claim 16, further comprising the steps of analyzing the stored information related to the operational and navigational issues experienced by the mobile robots, and generating maps and/or charts illustrating the frequency of problems a mobile robot or location is experiencing.

18. The method of claim 11, wherein the information regarding navigational issues comprises information regarding robot idle time caused by elevator delays, blocked pathways, and/or failed facility equipment.

19. The method of claim 11, wherein the set of business rules comprises information regarding at least one of mobile robot navigation pathways, mobile robot pathway properties, mobile robot pathway sensor settings, mobile robot sounds messages, mobile robot destination wait times, mobile robot locking point wait times, mobile robot lock point locations, mobile robot staging area locations, mobile robot elevator interactions, mobile robot minimum charging times, and scheduled mobile robot runs.

20. The method of claim 11, further comprising receiving, at the central server, operational status information of an elevator cabin.

21. The method of claim 11, wherein the data analysis module prioritizing the mobile robots operating at the various locations comprises the data analysis module ranking a first mobile robot at a first position in a prioritized list and the data analysis module ranking a second mobile robot at a second position in the prioritized list, wherein the first position is at a higher ranking in the prioritized list than the second position, the method further comprising the data analysis module modifying a ranking of the second mobile robot such that the second mobile robot is at a higher ranking in the prioritized list than the first mobile robot.

22. A system for managing and prioritizing for action fleets of mobile robots deployed at various locations, the system comprising:
   a central server receiving operational parameter data from a plurality of mobile robots operating at least one location, the operational parameter data representing operational and navigational issues experienced by the mobile robot, wherein the central server includes a data analysis module processing the operational parameter data and prioritizing the mobile robots based on the operational parameter data; and
   wherein the operational parameter data comprises information regarding operational and navigational issues experienced by the mobile robot; and
   wherein each of the mobile robots are prioritized relative to each of the other mobile robots at the various locations based on a severity of the operational and navigational issues experienced by each of the mobile robots; and
   wherein the data analysis module processes the operational data and prioritizes the mobile robots using a set of business rules that are location and mobile robot specific.

23. The system of claim 22, wherein the data analysis module generates a list prioritizing the mobile robots based on the operational parameter data and ranking them in order of severity for action by support staff.

24. The system of claim 23, wherein the list generated by the data analysis module is accessible using a web-based application, and wherein the list includes links to other information about the mobile robot and the location at which the mobile robot is operating.

25. The system of claim 22, wherein the data analysis module ranks a first mobile robot at a first position in a prioritized list and the data analysis module ranks a second mobile robot at a second position in the prioritized list, wherein the first position is at a higher ranking in the prioritized list than the second position, and wherein the data analysis module modifies a ranking of the second mobile robot such that the second mobile robot is at a higher ranking in the prioritized list than the first mobile robot.

26. A method of managing and prioritizing for action fleets of mobile robots deployed at various locations, the method comprising the steps of:
   receiving, at a central server, operational parameter data from a plurality of mobile robots operating at least one location, the operational parameter data representing operational and navigational issues experienced by the mobile robot;

analyzing, by a data analysis module at the central server, the operational parameter data for the mobile robots;

processing, by the data analysis module, the operational parameter data for the mobile robots using a set of business rules; and prioritizing, by the data analysis module at the central server, the mobile robots based on the operational parameter data and the set of business rules; and wherein the operational parameter data comprises information regarding operational and navigational issues experienced by the mobile robot; and wherein the data analysis module prioritizing the mobile robots operating at the various locations comprises prioritizing each of the mobile robots relative to each of the other mobile robots at the various locations based on a severity of the operational and navigational issues experienced by each of the mobile robots; and wherein the business rules are location and mobile robot specific.

27. The method of claim 26, further comprising the step of displaying, by a display associated with the data analysis module, a prioritized list, the prioritized list ranking the mobile robots in order of severity based on the operational parameter data for action by support staff.

28. The method of claim 27, wherein the prioritized list is accessible using a web-based application, and wherein the prioritized list includes links to other information about the mobile robot and the location at which the mobile robot is operating.

29. The system of claim 1, wherein the data analysis module ranks a first mobile robot at a first position in the prioritized list and the data analysis module ranks a second mobile robot at a second position in the prioritized list, wherein the first position is at a higher ranking in the prioritized list than the second position, the data analysis module modifies a ranking of the second mobile robot such that the second mobile robot is at a higher ranking in the prioritized list than the first mobile robot.

30. The method of claim 26, wherein the data analysis module prioritizing the mobile robots operating at the various locations comprises the data analysis module ranking a first mobile robot at a first position in a prioritized list and the data analysis module ranking a second mobile robot at a second position in the prioritized list, wherein the first position is at a higher ranking in a prioritized list than the second position, the method further comprising the data analysis module modifying a ranking of the second mobile robot such that the second mobile robot is at a higher ranking in the prioritized list than the first mobile robot.

* * * * *

UNITED STATES PATENT AND TRADEMARK OFFICE
CERTIFICATE OF CORRECTION

PATENT NO. : 8,886,390 B2
APPLICATION NO. : 13/624373
DATED : November 11, 2014
INVENTOR(S) : Wolfe et al.

It is certified that error appears in the above-identified patent and that said Letters Patent is hereby corrected as shown below:

Title Page, Item (72) Inventors should read:

--(72) Inventors: David G. Wolfe, Wexford, PA (US);
George F. Lucas, Pittsburgh, PA (US);
Mark Swaney, Pittsburgh, PA (US)--.

Signed and Sealed this
Twenty-third Day of June, 2015

Michelle K. Lee
*Director of the United States Patent and Trademark Office*

UNITED STATES PATENT AND TRADEMARK OFFICE
CERTIFICATE OF CORRECTION

Page 1 of 1

PATENT NO. : 8,886,390 B2
APPLICATION NO. : 13/624373
DATED : November 11, 2014
INVENTOR(S) : Wolfe et al.

It is certified that error appears in the above-identified patent and that said Letters Patent is hereby corrected as shown below:

Title Page, Item (72) Inventors should read:

--(72) Inventors: David G. Wolfe, Wexford, PA (US);
George F. Lucas, Pittsburgh, PA (US);
Mark Swaney, Pittsburgh, PA (US);
Spencer W. Allen, Wexford, PA (US)--.

This certificate supersedes the Certificate of Correction issued June 23, 2015.

Signed and Sealed this
Fifteenth Day of September, 2015

Michelle K. Lee
*Director of the United States Patent and Trademark Office*